United States Patent [19]

Bayer

[11] 4,126,517
[45] Nov. 21, 1978

[54] METHOD OF CONVERTING LIQUID MICRO-BIOLOGICAL SUBSTRATE AND APPARATUS FOR CARRYING OUT THE METHOD

[75] Inventor: Peter Bayer, Monthey, Switzerland

[73] Assignee: Giovanola Freres SA, Monthey, Switzerland

[21] Appl. No.: 612,847

[22] Filed: Sep. 12, 1975

[30] Foreign Application Priority Data

Sep. 19, 1974 [CH] Switzerland .................. 12706/74

[51] Int. Cl.² ............................................. C12B 1/14
[52] U.S. Cl. .................................. 195/109; 195/115; 195/142
[58] Field of Search .............. 195/109, 142, 143, 144, 195/104, 105, 115, 108, 139

[56] References Cited

U.S. PATENT DOCUMENTS

| | | | |
|---|---|---|---|
| 1,162,084 | 11/1915 | LaPorte | 123/41.3 |
| 1,873,146 | 8/1932 | Patch | 123/41.47 |
| 2,848,015 | 8/1958 | Roberts et al. | 138/121 |
| 3,223,595 | 12/1965 | Brewer | 195/115 X |
| 3,413,124 | 11/1968 | Akin | 426/16 |
| 3,630,848 | 12/1971 | Lefrancois | 195/142 |
| 3,743,582 | 7/1973 | Kitai et al. | 195/141 |
| 3,847,748 | 11/1974 | Gibson et al. | 195/109 |

Primary Examiner—Thomas G. Wiseman
Attorney, Agent, or Firm—Werner W. Kleeman

[57] ABSTRACT

A method of converting liquid micro-biological substrate is disclosed, as is an apparatus for carrying out the method. The liquid substrate is caused to flow along a duct having a cross-sectional area which alternately decreases and increases along the flow path to cause the pressure of the substrate to alternately decrease and increase. Preferably, gas is introduced into the substrate to promote the formation of bubbles of the gas in the substrate. The gas may be so introduced as to cause the substrate to flow through the duct and/or an impeller pump may be employed for this purpose.

13 Claims, 3 Drawing Figures

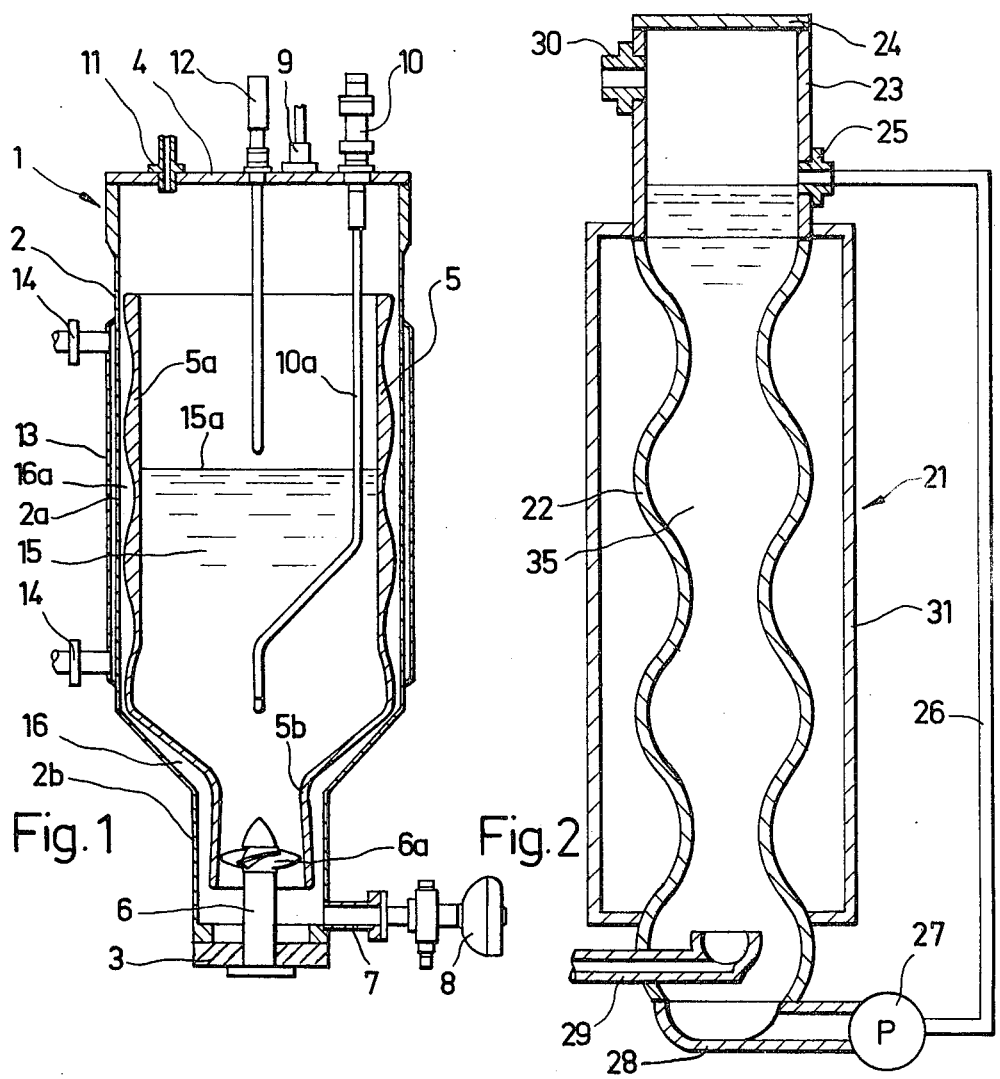
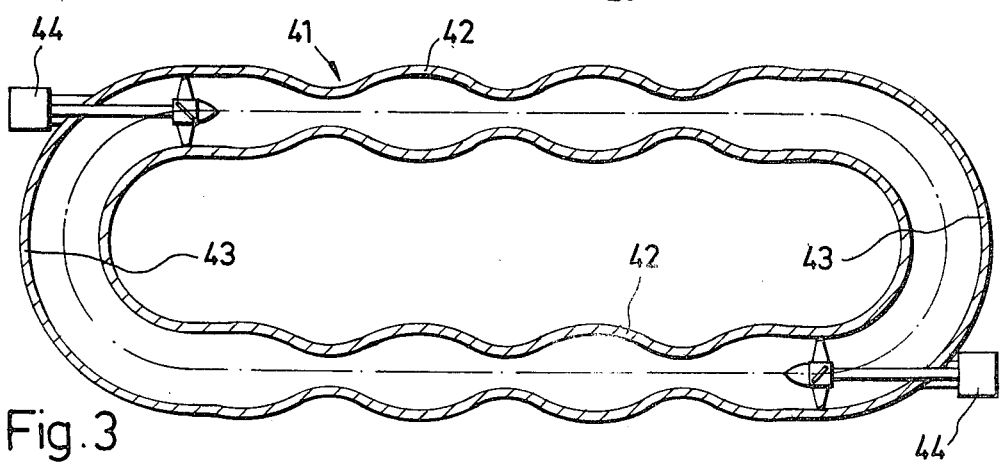

METHOD OF CONVERTING LIQUID MICRO-BIOLOGICAL SUBSTRATE AND APPARATUS FOR CARRYING OUT THE METHOD

BACKGROUND OF THE INVENTION

The present invention relates to a method of converting liquid microbiological substrate and apparatus for carrying out the method.

In the bio-chemical process technology, micro-organisms are frequently bred in a liquid nutrient substrate which is thereby converted. These conversions take place for example in a closed fermenter or in a bubble column, whilst in the case of aerobic processes a gas such as air or oxygen is introduced.

The apparatus employed for the conversion process should be such that optimal growth conditions result for the bacteria or fungii. It is known to generate a closed substrate circuit for the conversion process, in which the substrate continuously flows through a duct system. Employed as duct systems are vertically arranged fermenter devices, which are provided with a cylindrical outer shell in which a cylindrical inner shell is arranged. The substrate is then set in motion by a pump so that it rises between the outer and the inner shell and, at the top of the latter, overflows into the cavity bounded by the inner shell and flows back through this. In these circumstances, the fermenter device receives only such a quantity of substrate that a free space — which can serve as degasification zone — results in the upper part of the cavity bounded by the inner shell.

Some such known fermenter devices have the disadvantage that the breeding of cultures and the bio-chemical conversions often take an unduly long period.

It has now been found that the conversions can be accelerated in the case of anaerobic as well as aerobic processes, when the pressure of the substrate in the reaction zone alternationgly decreases and again increases along the flow path. In the case of anaerobic processes, the increase in the conversion speed is probably to be traced back to the fact that the cell walls of the micro-organisms are subjected by the pressure changes to a deformation movement, which promotes the exchange of material.

In the case of aerobic processes, the growth and reaction speed depends to a large extent upon the gas exchange of the micro-organisms, which is again dependent upon the quantity of gas liberated in the substrate and upon the size and the distribution of the gas bubbles. It has now been ascertained that aerobic processes, particularly, can be favourably influenced by pressure changes of the substrate. This might originate from the fact that gas bubbles change their diameter and their surface with changing substrate pressure, whilst turbulent gas flows can take place in the interior of the bubbles. This has the consequence, that the bubbles can more easily be opened on contact with the live cells.

SUMMARY OF THE INVENTION

According to one aspect of the present invention there is provided a method of converting liquid microbiological substrate comprising the step of causing the substrate to flow along a path extending through duct means defining a duct having a cross-sectional area which alternately decreases and increases along the flow path, the arrangement being such that the pressure of the substrate is caused to alternately decrease and increase.

According to another aspect of the present invention there is provided apparatus for converting liquid microbiological substrate, comprising means defining an elongate duct of alternately decreasing and increasing cross-sectional area along the duct.

BRIEF DESCRIPTION OF THE DRAWING

An embodiment of the present invention will now be described by way of example with reference to the accompanying drawing, in which:

FIG. 1 shows a longitudinal section through a vertically disposed fermenter device;

FIG. 2 shows a longitudinal section through a bubble column of another vertical fermenter device; and FIG. 3 shows a longitudinal section through a horizontally disposed fermenter device.

DESCRIPTION OF THE PREFERRED EMBODIMENTS

Referring now to the accompanying drawing, FIG. 1 shows a vertically disposed fermenter device, which serves as apparatus for the breeding of aerobic micro-organisms in a liquid nutrient substrate. The fermenter device 1 displays an outer shell 2 with a cylindrical portion 2a, to the lower end of which is connected a bottleneck-shaped portion 2b. The outer shell 2 is tightly closed at the end of the portion 2b by a detachable stopper 3. At the upper end of the fermenter device as shown in FIG. 1, the outer shell 2 is tightly closed by a detachable lid 4.

The outer shell 2, the bottom stopper 3 and the lid 4 together form a substantially air-tight vessel. Arranged in the interior thereof is an inner shell 5, which is provided with a portion 5a provided with a cylindrical interior surface co-axial with the outer shell portion 2a, and a bottleneck-shaped portion 5b. The latter extends generally parallel to the portion 2b of the outer shell 2, whilst a cavity is present between the two portions 2b and 5b. A small gap is likewise present between the exterior surface of the inner shell portion 5a and the interior surface of the outer shell portion 2a. The exterior surface of the inner shell portion 5a is provided with a sinuous profile, so that the cross-section of the gap is about two to three times smaller at the wave crests than at the wave valleys. The inner shell 5 is shorter than the outer shell 2 and is supported in such a manner that a cavity is present between its lower end and the bottom stopper 3 and between its upper end and the lid 4.

Attached to the bottom stopper 3 is an impeller pump 6 provided with an impeller wheel 6a, the rotational axis of which coincides with the axis of symmetry of the two shells 2 and 5. The pump 6 is arranged and constructed in such a manner that the impeller wheel 6a is disposed in the interior of the bottleneck-shaped inner shell portion 5b.

An outlet stub 7 with a cock 8 is furthermore inserted into the bottleneck-shaped outer shell portion 2a in the vicinity of the lower end of the device shown in FIG. 1.

The lid 4 is provided with a substrate feed stub 9 and a gas feed connection stub 10. The inner end thereof is connected with a gas feed pipe 10a, the mouth of which is disposed at about the level of the lower ends of the shell portions 2a and 5a. Furthermore, the lid 4 is provided with a gas outlet stub 11, which communicates with the interior beneath the lid 4. A probe 12 for the monitoring of the foam formation is inserted in the lid.

The outer shell 2 is surrounded in the middle region by a further shell 13, which at its upper and lower end displays connecting stubs 14. The two shells 2 and 13 together bound a gap, which is tightly closed off against the outside and which in operation of the fermenter device 1 is flowed through by cooling means.

The mode of operation of the fermenter 1 will now be described. For the operation, the vessel 2, 3 and 4, formed by the outer shell 2, by the bottom stopper 3 and by the lid 4, is about half filled with the substrate 15 to be converted, so that its liquid surface 15a in the inner shell 5 is disposed at about half the height of the inner shell portion 5a. In an aerobic process, gas, frequently oxygen or air, is additionally fed through the gas feed stub 10 and the gas feed pipe 10a. The substrate is then conveyed by the pump 6 in such a manner, that it flows downwardly through the bottleneck-like inner shell portion 5b, is deflected through 180° after the exit from the inner shell 5 and afterwards flows upwardly in the gap 16 between the two shells 2 and 5. When the upwardly flowing substrate reaches the upper rim of the inner shell 5, it again falls back into the interior space of the latter. The vessel 2, 3 and 4 thus together with the inner shell 5 forms a duct system for a closed substrate circuit. The gas exchange in that case takes place mainly in the gap 16, which thus forms the reaction zone. In the upper reaction zone portion 16a which is bounded by the shell portions 2a and 5a, the cross-section alternatingly decreases and again increases along the flow path due to the wave-shaped profile of the inner shell section 5a. Due to the conservation of mass, or in other words due to the continuity of flow, the speed of the latter then also changes. This has the consequence according to the equation of Bernoulli, that the substrate pressure becomes smaller at those locations, where the reaction zones 16a are of smaller cross-section. The alternating pressure change in the substrate on flowing through the upper portion of the reaction zone effects a corresponding alternating deformation motion of the cells of the micro-organisms, whereby the exchange of material is promoted. The magnitude and the internal pressure of the gas bubbles as well as the gas solubility of the substrate are also changed by the changes of the substrate pressure, which likewise facilitates the growth of the micro-organisms and the conversions of the substrate then taking place.

The gas is fed to the substrate 15 before this flows past the impeller wheel 6a of the pump 6. The latter then serves not only for the conveying of the substrate but also simultaneously for the dispersing of the gas, so that homogeneously distributed gas bubbles arise. The distribution of the gas bubbles is still enhanced thereby in that the impeller wheel 6a and the subsequent sharp deflection of the substrate around the lower rim of the inner shell 5 causes a turbulence in the flow, which then in accordance with the magnitude of the Reynolds number remains maintained in the entire reaction zone 16 or again decays after the traverse of a section thereof.

When the substrate has flowed through the reaction zone and again drops back into the interior space of the inner shell 5, it can give off a part of the gas present, which then flows away through the gas outlet stub 11. The free space above the liquid surface 15a thus serves as degasification zone.

The number and size of the gas bubbles formed can be optimized by suitable metering of the gas feed and the choice of the speed of rotation of the pump. The bubble formation is to be controlled in such a manner, that not so much foam is formed in the degasification zone, that the course of the process is impaired. When the conversion is completed, the substrate can be withdrawn through the outlet stub 7 and the cock 8. It is however also possible to operate the fermenter device continuously and to feed fresh substrate to the vessel 2, 3 and 4 continually through the stub 9 and to withdraw substrate through the stub 7.

In the case of an anaerobic process, the fermenter device can of course also be operated without gas feed.

The apparatus illustrated in the FIG. 2 displays as a principal component a vertical bubble column 21, which is provided with a hollow body 22, which forms the reaction zone and the diameter of which alternatingly decreases and increases. A hollow cylinder 23, which is closed off by a lid 24 at the top, connects to the upper end of the hollow body 22. The hollow cylinder 23 is provided in the proximity of its lower end with a stub 25, which is connected through a pipe duct 26 with a pump 27. From the latter, a connnection 28 leads to the lower end of the hollow body 22 somewhat above the mouth of the pipe duct 28. A gas outlet stub 30 is inserted at the upper end of the hollow cylinder 23. The hollow body 22 forming the reaction zone is furthermore surrounded by a schematically illustrated cooling jacket 31. Furthermore, gratings can still be arranged in the hollow body 22.

In operation, the pump 27 can convey the substrate 35 in such a manner, that it rises upwardly in the bubble column up to the stub 25 and flow back from this through the duct 26 to the pump 27. On entry into the hollow body 22, the substrate is sharply deflected through an angle of about 90°, so that a turbulent flow can develop in the region of the mouth of the gas feed duct 29, so that the fed gas is well dispersed. When the substrate 35 flows upwardly through the hollow body 22, its pressure alternatingly decreases and again increases along the flow lines, whereby its conversion is accelerated as already described.

In this example of embodiment of the apparatus, the substrate duct system is thus formed essentially by the hollow body 22 and the pipe duct 26.

The pump 27 can of course also be constructed in such a manner, that it pumps the substrate upwardly through the duct 26. In this case, the substrate and the gas bubbles in the hollow body then move in opposite directions.

It is however also possible to omit the pump 27. In this case, the flow movement of the substrate is generated by the fed gas rising up in the hollow body 22.

FIG. 3 shows as a further example of another embodiment of the invention, a horizontally disposed fermenter device 41, of which only the most important elements are illustrated. The fermenter device 41 is provided with two pipe-like hollow bodies 42 lying in a common plane. The two hollow bodies 42 forming the reaction zones display cross-sections alternatingly decreasing and increasing along the flow path and are connected with one another at their ends by two pipe ends 43. The two hollow bodies 42 and the two pipe bends 42 thus together form a duct system for a closed circuit. The substrate flow can perhaps be generated by two pumps 44. In case an aerobic process is concerned, gas can be fed to the substate at the pumps and again be withdrawn after the flowing through of the reaction zones.

In the case of the examples of the invention described above, the duct systems form closed substrate circuits. In case the conversion to be undertaken only requires a short time, duct systems can of course also be employed, which are not constructed as closed circuits and in which the substrate is fed in at one end and after flowing through of a reaction zone is withdrawn at the other end.

I claim:

1. In a fermentation process wherein liquid microbiological substrate containing microorganisms is recirculated at a constant velocity through a reaction zone to promote the growth of said microorganisms and thereafter at a constant but lower velocity through a post reaction zone to effect release of gases contained in the liquid, the improvement comprising the steps of:
   a. providing a reaction zone in the form of a duct including at least one liquid contacting surface having a sinuous configuration with alternate crests and valleys when viewed in cross-section, said alternate crests and valleys being of uniform cross-section, respectively;
   b. directing said liquid microbiological substrate containing said microorganisms through said reaction zone and over said sinuous configured surface and alternately increasing and decreasing the velocity of said liquid as it passes over said crests and valleys of said sinuous surface, respectively; and
   c. simultaneously effecting a series of pressure fluctuations in said liquid as said liquid passes over the sinuous configured surface in said reaction zone, said pressure fluctuations and corresponding velocity changes imparted to said liquid being instrumental in promoting a favorable growth of microorganisms.

2. A method as defined in claim 1, comprising the additional step of introducing gas into the substrate to promote the formation of bubbles of the gas in the substrate on the latter flowing through the duct.

3. A method as defined in claim 2, wherein the step of introducing the gas into the substrate causes the substrate to flow through the duct.

4. A method as defined in claim 1, comprising the step of employing an impeller pump to cause the substrate to flow through the duct and simultaneously to disperse the gas in the substrate.

5. A method as defined in claim 1, comprising the step of causing the flow of the substrate to be turbulent in at least part of the duct.

6. A method as defined in claim 5, comprising the step of causing turbulence by abruptly deflecting the direction of flow of the substrate upstream of the duct.

7. A method as defined in claim 1, wherein said method comprises an aerobic process and including the steps of dispersing a gas into the liquid substrate prior to entry of the substrate into said duct such that gas exchange with the substrate occurs during the passage thereof through said duct and withdrawing the gas evolved from the substrate after the passage thereof through said duct.

8. A method as defined in claim 7 wherein said dispersed gas contains oxygen.

9. Fermentation apparatus for the breeding of microorganisms contained in a liquid nutrient substrate comprising vessel means forming a closed circuit flow path for the liquid substrate containing microorganisms, said vessel means including duct means defining a reaction zone including at least one liquid contacting surface having a sinuous configuration with alternate crests and valleys when viewed in cross-section, said alternate crests and valleys being of uniform cross-section, respectively, said duct means comprising substantially concentric inner and outer shells forming an annular gap therebetween, at least one of said shells having said sinuous configuration, means arranged before said duct means for introducing a gas into the substrate and means for recirculating said liquid substrate along said flow path, through said reaction zone and over said sinuous configured surface for uniformly and alternately decreasing and increasing the pressure on the substrate, whereby the alternating pressure changes on the substrate facilitate the breeding and growth of the microorganisms.

10. The apparatus as defined in claim 9, including means arranged before said duct means for introducing a gas into the substrate.

11. The apparatus as defined in claim 10 wherein said duct means comprises substantially concentric inner and outer shells forming an annular gap therebetween, at least one of said shells having said sinuous configuration.

12. The apparatus as defined in claim 11, wherein the smallest cross-sectional area of said gap is between about 2 to 3 times smaller than the largest cross-sectional area of said gap.

13. The apparatus as defined in claim 9, wherein said duct means comprises a substantially tubular member.

* * * * *